US00PP18894P3

(12) United States Plant Patent
Parham

(10) Patent No.: US PP18,894 P3
(45) Date of Patent: Jun. 10, 2008

(54) ***CHRYSANTHEMUM* PLANT NAMED 'SMOOTHIE TIME'**

(50) Latin Name: *Chrysanthemum morifolium*
Varietal Denomination: Smoothie Time

(75) Inventor: Ruth Parham, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 66 days.

(21) Appl. No.: 11/490,455

(22) Filed: Jul. 20, 2006

(65) Prior Publication Data

US 2007/0033690 P1 Feb. 8, 2007

Related U.S. Application Data

(60) Provisional application No. 60/703,342, filed on Jul. 28, 2005.

(51) Int. Cl.
*A01H 5/00* (2006.01)

(52) U.S. Cl. ..... Plt./297

(58) Field of Classification Search ..... Plt./297
See application file for complete search history.

(56) References Cited

U.S. PATENT DOCUMENTS

| | | | |
|---|---|---|---|
| PP15,486 P3 | 1/2005 | Boeder | Plt./286 |
| PP15,535 P3 | 2/2005 | Boeder | Plt./294 |

*Primary Examiner*—Kent Bell
*Assistant Examiner*—Annette H Para
(74) *Attorney, Agent, or Firm*—Winston & Strawn, LLP

(57) ABSTRACT

A new variety of *Chrysanthemum* plant named 'Smoothie Time', having bright pink single flowers with spoon tips and a green disc. 'Smoothie Time' has a medium to tall vigor with a good foliage presentation.

1 Drawing Sheet

Latin name of the genus and species: Botanical classification: *Chrysanthemum morifolium.*

Variety denomination:

The new *Chrysanthemum* variety denomination is 'Smoothie Time'.

BACKGROUND OF THE INVENTION

The present invention comprises a new and distinct cultivar of *Chrysanthemum* botanically known as *Chrysanthemum morifolium,* and referred to by the cultivar name 'Smoothie Time'.

'Smoothie Time', identified as 22111-0, originated from a cross made in a controlled breeding program in Chichester, West Sussex, United Kingdom. The female parent of the new variety is 'Stereophonics', (U.S. Plant Pat. No. 15,535) and the male parent is an undistributed, unpatented seedling identified as 21012-0. The new variety 'Smoothie Time' has been asexually reproduced by vegetative cuttings in Chichester, West Sussex, United Kingdom and the distinguishing characteristics are retained through successive generations of asexual reproduction.

BRIEF SUMMARY OF THE INVENTION

'Smoothie Time' is a pot type of *Chrysanthemum* plant variety having medium to large striking pink single flowers with spoon tips.

Comparison with Female Parent

Plants of the new *Chrysanthemum* variety 'Smoothie Time' are dissimilar to the female parent 'Stereophonics' in plant habit and growth rate. In side-by-side comparisons in Chichester, West Sussex, United Kingdom, under commercial practice, plants of the new *Chrysanthemum* variety 'Smoothie Time' differed from plants of the female parent 'Stereophonics' in the following characteristics:

1. The new variety 'Smoothie Time' produces pink single flowers with a spoon tip whereas the female parent 'Stereophonics' produces white single flowers.
2. Plants of the new variety 'Smoothie Time' have smaller and shorter inflorescence than plants of the female parent 'Stereophonics'.

Comparison with Male Parent

Plants of the new *Chrysanthemum* variety 'Smoothie Time' are dissimilar to the male parent 21012-0 in plant habit and growth rate. In side-by-side comparisons in Chichester, West Sussex, United Kingdom, under commercial practice, plants of the new *Chrysanthemum* variety 'Smoothie Time' differed from plants of the male parent 21012-0 in the following characteristics:

1. The new variety 'Smoothie Time' produces dark pink single flowers with spoon tips whereas the male parent 21012-0 produces light pink single flowers with spoon tips.
2. Plants of the new variety 'Smoothie Time' have larger and taller inflorescence than plants of the male parent 21012-0.
3. Plants of the new variety 'Smoothie Time' have a quicker response than plants of the male parent 21012-0.

Comparisons with Abba

Plants of the new *Chrysanthemum* variety 'Smoothie Time' are similar to plants of the variety 'Abba' (U.S. Plant Pat. No. 15,486) in plant habit and growth rate. However, in side-by-side comparisons in Chichester, West Sussex, United Kingdom, under commercial practice, plants of the new *Chrysanthemum* variety 'Smoothie Time' differed from plants of 'Abba' in the following characteristics:

1. The new variety 'Smoothie Time' produces pink single flowers with spoon tips whereas 'Abba' produces dark pink single flowers with spoon tips.
2. Plants of the new variety 'Smoothie Time' have larger and taller inflorescence than plants of 'Abba'.

BRIEF DESCRIPTION OF ILLUSTRATIONS

Typical specimens of the plant and flowers for the new *Chrysanthemum* variety 'Smoothie Time' are shown in the accompanying digital photograph. The colors shown are as true as possible within the usual limits of this kind of illustration.

FIG. 1 is a whole plant view of the new variety 'Smoothie Time' grown in a pot. The plant shown in the illustration and described below is 56 days from the onset of Short Days.

DETAILED BOTANICAL DESCRIPTION

The following description of the new *Chrysanthemum* variety 'Smoothie Time' is of plants grown in a greenhouse in Chichester, West Sussex, United Kingdom, in the month of October. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 25° C. during the day under light conditions of about 2,500 Lux. The plants respond well to the use of growth retardant, such as one B9 treatment at about 2 grams per liter. To produce a commercial product, the plants may be pinched once with the center bud removed. The typical container size for commercial growth is 1 liter. It has been observed that the shelf life of the new variety is about 28 days with a response time of about 7.5 weeks. The new variety is suitable for growth in a temperature range of 15° C. to 25° C.

The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 19.
Width (cm): 26.
Stem:
- *Length* (*cm*).—5.5.
- *Diameter* (*cm*).—0.5.
- *Texture.*—Slightly pubescent.
- *Color.*—138B.

Branching characteristics: Upright and free branching.
Lateral branches:
- *Length* (*cm*).—10.
- *Diameter* (*cm*).—0.4.
- *Texture.*—Slightly pubescent.

Number of breaks from Pinch: 6.
Response time: 52 days.
Vigor: Medium/Tall.
Shelf life: 28 days.
Life of blooms: 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9@2, 21 and 28 days after sticking unrooted cuttings.
The plants were grown for two weeks in Long Day conditions (20 hours of light) and then transferred to Short Day conditions (13 hours of dark).
Propagation:
- *Type.*—Vegetative propagation via stem cuttings.
- *Time to rooting.*—14 days with soil temperatures of 18° C.
- *Rooting habit.*—After 7 Long Days, the first roots emerge and form root primordia. In 14 Long Days, a complete root system is developed.

Foliage

Number of leaves per lateral branch: 10.
Compound or single: Single.
Arrangement of leaves: Alternate.
- *Shape of leaf.*—Typically 5 lobed.
- *Size of leaf.*—Width (cm): 5.5. Length (cm): 7.5.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: slightly pubescent. Bottom: Pubescent.

Petiole:
- *Color.*—137C.
- *Length* (*cm*).—2.
- *Diameter* (*cm*).—0.4.
- *Surface.*—Slightly pubescent.

Venation: Net, prominent lateral and mid-veins at underside.
- *Color.*—Upper side: 138B. Under side: 138B.

Color:
- *Mature leaf, upper side.*—137C; under side: 138B.
- *Young leaf, upper side.*—137B; under side: 138B.

Flower

Flower appearance: Matte.
Flower type: Single with spoon tips.
Flower form: Flat.
Flower shape: Circular.
Flowering habit: Cyme.
Number of blossoms per branch: 5.
Typical and observed flowering season: January to December.
Inflorescence form: Cyme.
- *Depth of fully expanded blossoms* (*cm*).—1.
- *Diameter of fully expanded blossoms* (*cm*).—7.5.

Phyllaries:
- *Number.*—22.
- *Color.*—138B.
- *Length* (*cm*).—1.8.
- *Width* (*cm*).—0.2.
- *Texture/Appearance.*—Slightly pubescent.

Peduncle:
- *Length* (*cm*).—10.
- *Diameter* (*cm*).—0.4.
- *Angle from stem* (*degrees*).—10.

*Color.*—138A.
*Surface.*—Slightly pubescent.
*Habit.*—Slightly undulating.
*Strength.*—Strong.

Pedicel:
*Length.*—terminal (cm): 3.5; lateral (cm): 4.5.
*Diameter (cm).*—0.2.
*Color.*—138A.
*Surface.*—slightly pubescent.
*Habit.*—Straight.
*Strength.*—Strong.

Ray florets:
*Form/shape.*—Straight with parallel edges to the central mid vein.
*Texture/Appearance.*—Matte.
*Number per flower.*—35.
*Length (cm).*—3. Width of spoon tip (cm): 0.6. Width of corolla (cm): 0.2.
*Apex.*—Rounded.
*Base.*—Tapered.
*Margin.*—Entire.

Disc florets:
*Form/shape.*—cylindric.
*Texture/Appearance.*—Shiny.
*Number per flower.*—200.
*Length (cm).*—0.6; Width (cm): 0.1.
*Diameter of disc (cm).*—1.5.

Fragrance: None.

Flower bud (at onset of color):
*Length (cm).*—1.
*Diameter (cm).*—1.2.
*Form/Shape.*—Globular.

General flower color:
1. *Ray florets, upper side.*—Immature: 68A. Mature: 68A. Older/Fading: 68B.
2. *Ray florets, under side.*—Immature: 68A. Mature: 68B. Older/Fading: 68B.
3. *Ray florets, tube, outer side.*—68C.
4. *Disc florets.*—Immature: 144B. Mature: 145A. Older/Fading: 3A.
4. *Bud.*—68A.

Flower progression with age: There is no change with the flower form but there is a slight color fading with age.

Reproductive Organs

Gynoecium present on Ray florets.

Ray florets per individual flower: Pistillate.
*Pistil number.*—35.
*Stigma color.*—154A.
*Stigma shape.*—Forked.
*Style color.*—154B.
*Style length (cm).*—0.3.

Androecium present on Disc florets only: Staminate
*Stamen number.*—150.
*Anther shape.*—globular.
*Anther color.*—154B.
*Pollen color.*—14B.
*Pollen quantity.*—Abundant.

Fruit and Seeds: None observed.

What is claimed is:

1. A new and distinct variety of *Chrysanthemum* plant, substantially as described and illustrated herein.

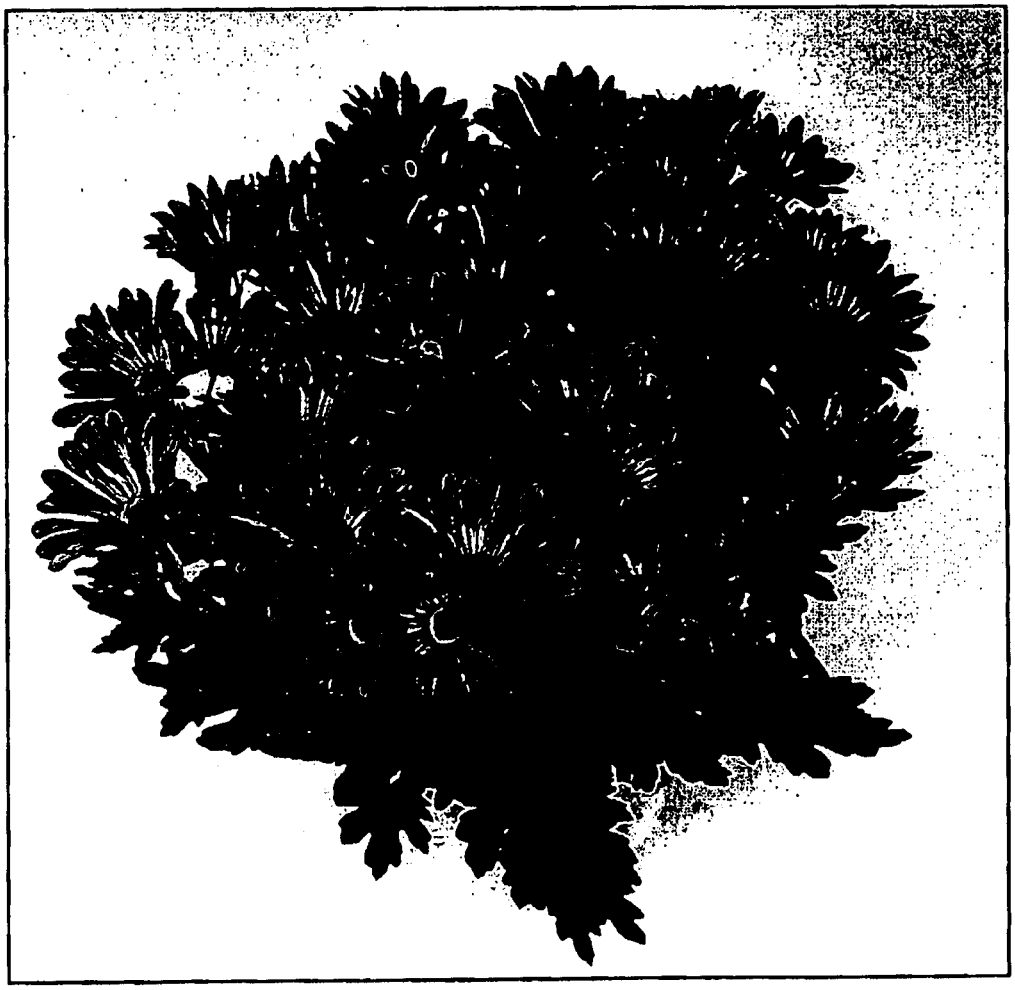

* * * * *